United States Patent
Watanabe et al.

(10) Patent No.: US 6,930,201 B2
(45) Date of Patent: Aug. 16, 2005

(54) PROCESS FOR PRODUCING METHACRYLIC ACID

(75) Inventors: Seigo Watanabe, Hiroshima (JP); Motomu Oh-Kita, Hiroshima (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 10/450,712

(22) PCT Filed: Dec. 19, 2001

(86) PCT No.: PCT/JP01/11117

§ 371 (c)(1), (2), (4) Date: Nov. 5, 2003

(87) PCT Pub. No.: WO02/051787

PCT Pub. Date: Jul. 4, 2002

(65) Prior Publication Data

US 2004/0073062 A1 Apr. 15, 2004

(30) Foreign Application Priority Data

Dec. 25, 2000 (JP) ........................... 2000-392997

(51) Int. Cl.$^7$ .............................. C07C 51/16
(52) U.S. Cl. .................. 562/535; 562/531; 562/532; 562/598
(58) Field of Search ................. 562/512, 517, 562/522, 523, 531, 532, 534, 535, 598

(56) References Cited

FOREIGN PATENT DOCUMENTS

| EP | 0005769 | * | 5/1979 |
| GB | 1473035 | * | 5/1977 |
| JP | 49-109316 | | 10/1974 |
| JP | 6-91172 | | 4/1994 |
| JP | 9-75740 | | 3/1997 |

* cited by examiner

Primary Examiner—Johann Richter
Assistant Examiner—Karl Puttlitz
(74) Attorney, Agent, or Firm—Armstrong, Kratz, Quintos, Hanson & Brooks, LLP

(57) ABSTRACT

In a method of producing methacrylic acid by passing a material gas containing methacrolein, oxygen and water vapor through a reactor packed with a catalyst containing as the main component a compound oxide containing molybdenum and phosphorus, a concentration of methacrolein in the material gas is controlled in a range of 4 to 6.5 vol %, a molar ratio of the water vapor to the methacrolein in the material gas is controlled in a range of 1 to 2, and a space velocity of the material gas to the catalyst-packed layer is controlled in a range of 500 to 750 $h^{-1}$, whereby deterioration of the catalyst is effectively inhibited.

5 Claims, No Drawings

PROCESS FOR PRODUCING METHACRYLIC ACID

TECHNICAL FIELD

The present invention relates to a method of producing methacrylic acid, and more particularly, it relates to a method of producing methacrylic acid by subjecting methacrolein to gas phase contact oxidation with molecular oxygen.

BACKGROUND ART

A method of producing methacrylic acid by subjecting methacrolein to gas phase contact oxidation on a catalyst comprising a compound oxide containing molybdenum and phosphorous as essential components is widely known and is also used on an industrial scale. In this case, methacrylic acid is often produced at a reaction temperature of 250 to 400° C., using of a catalyst as a fixed bed.

The catalyst for use in such a gas phase contact oxidation reaction is used for a relatively long time, but usually the catalyst deteriorates with time. Causes of the degradation of the catalyst include reduction of a catalyst component, sublimation and flying of a catalyst component, change in a crystalline phase in a catalyst structure, and the like.

As for methods for regenerating the thus deteriorated catalyst, a variety of propositions have been made. For example, Japanese Patent Laid-open No. 58-156351 discloses a method in which the deteriorated catalyst is treated at a temperature of 70 to 240° C. in a gaseous stream having a water vapor partial pressure of 10 vol % or more, and Japanese Patent Laid-open No. 6-7685 discloses a method in which the deteriorated catalyst is thermally treated under a stream of an oxidizing gas containing 0.1 vol % or more of molecular oxygen at a temperature of 300 to 410° C. for 0.5 to 50 hours. From an industrial viewpoint, however, it can be considered that it is desired to minimize the frequency of regenerating the deteriorated catalyst, because it is quite inconvenient to regenerate the catalyst each time it deteriorates and the production of methacrylic acid must be temporarily suspended every such an occasion.

That is, from an industrial viewpoint, there is desired the method of producing methacrylic acid while the deterioration of the catalyst is inhibited as much as possible, rather than the method of regenerating the deteriorated catalyst.

Furthermore, as for a catalyst that is resistant to the deterioration and has a long catalyst life, and a method for producing the same, numerous propositions have been made, for example, as in Japanese Patent Laid-open No. 5-31368. However, a level of the inhibition of the catalyst deterioration is not necessarily sufficient in industrial practice, and further technological innovation is desired. Moreover, all of these propositions only demonstrate that a deterioration rate is slightly reduced as compared with the catalyst by the conventional production methods under the same reaction conditions, and they do not refer to a method for effectively inhibiting the deterioration of the catalyst by controlling reaction conditions within specific ranges.

In addition, as the reaction conditions in producing methacrylic acid by passing a material gas containing methacrolein, oxygen and water vapor through a reactor packed with a compound oxide catalyst containing molybdenum and phosphorus, the following are known.

That is, Japanese Patent Laid-open No. 9-75740 describes that a concentration of methacrolein in a reaction material gas is in a range of 1 to 10% and a ratio of oxygen to methacrolein is about 1 to 5, and a space velocity of the material gas is preferably in a range of 500 to 5,000 $h^{-1}$, and water vapor or the like can be used as a diluting gas. In examples described in this publication, a material gas having a composition of 4 mol % of methacrolein, 12 mol % of oxygen, 17 mol % of water vapor and the balance of nitrogen is passed through a reactor at a space velocity (STP standard) of 670 $h^{-1}$ so that methacrolein may be subjected to the contact oxidation reaction.

Furthermore, Japanese Patent Laid-open No. 9-313943 describes that an appropriate contact time of the material gas is 1 to 20 seconds, and as for the composition of the material gas, 0.2 to 4 mols of molecular oxygen and 1 to 20 mols of water vapor are used with respect to 1 mol of methacrolein. In examples described in this publication, a material gas having a composition of 5 mol % of methacrolein, 12 mol % of oxygen, 30 mol % of water vapor and 53 mol % of nitrogen is passed at a space velocity of 1,400 $h^{-1}$, or a material gas having a composition of 3.2 mol % of methacrolein, 16.4 mol % of oxygen, 19.4 mol % of water vapor and 61 mol % of nitrogen is passed at a space velocity of 2,060 $h^{-1}$ so that methacrolein may be subjected to the contact oxidation reaction.

However, the reaction conditions described in Japanese Patent Laid-open No. 9-75740 and Japanese Patent Laid-open No. 9-313943 are reaction conditions in a case where a long-life catalyst is used, and the publications only disclose very wide ranges of the material gas compositions and the space velocities. These publications do not suggest techniques for inhibiting the deterioration of the catalyst by adjustment of the material gas composition and the space velocity anywhere. Moreover, in a case where methacrolein is subjected to the contact oxidation reaction using the material gas composition and the space velocity specifically described in these publications, the deterioration of the catalyst cannot be effectively inhibited.

DISCLOSURE OF THE INVENTION

An object of the present invention is to provide a novel method of producing methacrylic acid in which deterioration of a catalyst is effectively inhibited by controlling a reaction condition.

The present invention relates to a method of producing methacrylic acid by passing a material gas containing methacrolein, oxygen and water vapor through a reactor packed with a catalyst containing as the main component a compound oxide containing molybdenum and phosphorus, wherein a concentration of methacrolein in the material gas is in a range of 4 to 6.5 vol %, a molar ratio of the water vapor to the methacrolein in the material gas is in a range of 1 to 2, and a space velocity of the material gas to the catalyst-packed layer is in a range of 500 to 750 $h^{-1}$.

BEST MODE FOR CARRYING OUT THE INVENTION

In the present invention, reaction conditions in producing methacrylic acid by subjecting methacrolein to gas phase contact oxidation on a catalyst, namely a material gas composition and a space velocity of a material gas to a catalyst layer, are controlled within specific limits, whereby deterioration of the catalyst, particularly reduction in catalyst activity is effectively inhibited. It is generally considered that a deterioration rate of the catalyst is roughly dependent on a frequency in the use of the catalyst, i.e. a reaction amount per unit time. However, the present inventors have found that in this reaction, a degradation behavior of the catalyst noticeably varies depending on the material gas composition and the space velocity of the material gas to the catalyst layer even if the reaction amount of methacrolein per unit time per unit the catalyst weight is the same, and they have also found that the degradation of the catalyst can be effectively inhibited by controlling the material gas composition and the space velocity of the material gas to the catalyst layer within specific limits.

Hereinafter, a method for producing methacrylic acid of the present invention will be described.

A catalyst for use in the present invention comprises a compound oxide containing molybdenum and phosphorus as essential components.

Specifically, the catalyst preferably has a composition expressed by the following general formula (I):

$$Mo_aP_bCu_cV_dX_eY_fO_g \quad (I)$$

wherein Mo, P, Cu, V and O represent molybdenum, phosphorus, copper, vanadium and oxygen, respectively; X represents at least one element selected from the group consisting of iron, cobalt, nickel, zinc, magnesium, calcium, strontium, barium, titanium, chromium, tungsten, manganese, silver, boron, silicon, aluminum, gallium, germanium, tin, lead, arsenic, antimony, bismuth, niobium, tantalum, zirconium, indium, sulfur, selenium, tellurium, lanthanum and cerium; Y represents at least one element selected from the group consisting of potassium, rubidium, cesium and thallium; a, b, c, d, e, f and g each represents an atom ratio of each element, and when a=12, $0.1 \leq b \leq 3$, $0.01 \leq c \leq 3$, $0.01 \leq d \leq 3$, $0 \leq e \leq 3$ and $0.01 \leq f \leq 3$; and g represents a ratio of an oxygen atom required for satisfying a valence of each component.

In the present invention, a method of producing the catalyst comprising the compound oxide containing molybdenum and phosphorus as the essential components should not be limited to a specific method, and a variety of conventionally well-known methods such as a coprecipitation method, an evaporation to dryness method and an oxide mixing method can be used as long as the components are not noticeably unevenly distributed. Specifically, a method can be shown as an example in which a necessary amount of a raw material containing the constituent elements of the compound oxide is appropriately dissolved or suspended in a solvent such as water, and the resulting mixture solution or aqueous slurry is evaporated to dryness, ground and molded as required, and then treated with heat to obtain the catalyst. Usually, the heat treatment is preferably carried out under a stream of oxygen, air or nitrogen at 200 to 500° C. for 1 to 30 hours.

In the present invention, the raw material for use in preparation of the catalyst is not specifically limited, and nitrates, carbonates, acetates, ammonium salts, oxides, halides and the like of the elements can be used in combination. For example, as a molybdenum raw material, there can be used ammonium paramolybdate, molybdenum trioxide, molybdic acid, molybdenum chloride or the like. As a phosphorus raw material, there can be used orthophosphoric acid, metaphosphoric acid, diphosphorus pentoxide, pyrophosphoric acid, ammonium phosphate or the like.

The catalyst for use in the present invention may be an unsupported molded catalyst, but it may also be supported on an inert support such as silica, alumina, silica-alumina or silicon carbide, or may be diluted therewith and then used.

In the method for producing methacrylic acid of the present invention, the deterioration of the catalyst is effectively inhibited by controlling the reaction condition under which methacrylic acid is produced by subjecting methacrolein to gas phase contact oxidation in the presence of the catalyst described above. Hereinafter, the reaction condition of the present invention will be described in detail.

The reaction is usually carried out on a fixed bed. A catalyst layer may have one layer, or two or more layers. If the catalyst layer has two layers, for example, a method can be employed in which a front layer is packed with a mixture of the catalyst and the inert support, and a rear layer is packed with the catalyst alone.

For the material gas, a gas containing methacrolein, oxygen and water vapor is used.

A concentration of methacrolein in the material gas is in a range of 4 to 6.5 vol % (4 to 6.5 mol %), and is preferably 4.5 vol % or more and preferably 6 vol % or less. Generally, if the concentration of methacrolein is too low, the amount of methacrylic acid produced per unit time decreases, which is not preferable from an industrial viewpoint. On the other hand, if the concentration of methacrolein is too high, a molar ratio of oxygen/methacrolein must be considerably reduced to put the material gas composition outside an explosive range, which is not preferable in preventing the deterioration of the catalyst by reduction. However, it is not just for this reason that the concentration of methacrolein in the material gas is strictly limited in the present invention, but because a sufficient catalyst deterioration inhibiting effect can be obtained by controlling the concentration of methacrolein within this range along with various conditions described later.

The concentration of oxygen in the material gas can be varied within a broad range, and is preferably 5 mol % or more in that the deterioration of the catalyst by reduction is sufficiently inhibited, and preferably 15 mol % or less in terms of safety. If the concentration of oxygen is too high, a material gas composition may fall within an explosive range. An oxygen source, air is preferably used from an economic viewpoint, but air enriched with pure oxygen, pure oxygen or the like may be used as necessary.

A molar ratio (volume ratio) of water vapor to methacrolein in the material gas is in a range of 1 to 2, and is preferably 1.5 or more and preferably 1.9 or less. By controlling the concentration of water vapor within this range, not only high selectivity of methacrylic acid, but also a sufficient catalyst deterioration inhibiting effect can be obtained.

It is to be noted that the material gas may contain an inert gas such as nitrogen and carbon dioxide, and may contain impurities such as a lower saturated aldehyde, which do not substantially influence the reaction, in a low dose.

The space velocity of the material gas to the catalyst-packed layer is in a range of 500 to 750 $h^{-1}$, and is preferably 550 $h^{-1}$ or more and preferably 700 $h^{-1}$ or less. If the space velocity is too low, an efficiency of removing heat of the reaction by the passing of the gas is poor, and consequently a hot spot (local overheating) is generated in the catalyst layer to disturb a safe operation on the other hand, if the space velocity is too high, the deterioration rate of the catalyst increases even if the concentration of methacrolein in the material gas is reduced to decrease a reaction amount of methacrolein per unit time per unit the catalyst weight. That is, the space velocity is set to be within this range, and then the material gas composition is set to be within the above range while considering a production amount of methacrylic acid, safety and the like, whereby methacrylic acid can be produced while effectively inhibiting the deterioration of the catalyst.

The space velocity referred to herein is a value obtained by dividing a volume (volume at 0° C. and 1 atm) of the material gas supplied to the catalyst layer per unit time by a volume of the catalyst layer, and a unit of the space velocity is a reciprocal of time. For example, when the volume of the catalyst layer is 1 liter and the material gas is supplied thereto at a rate of 600 liters per hour, the space velocity is 600 $h^{-1}$.

Furthermore, the volume of the catalyst layer referred to herein denotes a volume in the reactor substantially occupied by the catalyst packed in the reactor. It is to be noted that if a catalyst and an inert support are previously mixed in a part or all of the catalyst layer or if a catalyst is supported on an inert support, the volume of the catalyst layer denotes a volume occupied by a mixture of a catalyst and an inert support. However, if a front stage and/or a rear stage of the catalyst layer is packed with an inert support (substantially inert solid material), the volume of the inert support is not included in the volume of the catalyst.

A reaction pressure is preferably in a range of an atmospheric pressure to a pressure of several atmospheres. A reaction temperature is preferably in a range of 230 to 400° C., particularly preferably 250 to 350° C.

EXAMPLES

Hereinafter, the present invention will be described in detail with referent to the examples, but the present invention is not limited to the examples.

The term "parts" described in the following examples and comparative examples mean parts by weight. A reaction test analysis was carried out by a gas chromatography.

It is to be noted that a conversion of methacrolein and a selectivity of produced methacrylic acid are defined as follows:

the conversion of methacrolein (%)=($B/A$)×100 the selectivity of methacrylic acid (%)=($C/B$)×100 wherein A represents the number of moles of supplied methacrolein, B represents the number of moles of reacted methacrolein, and c represents the number of moles of produced methacrylic acid.

Example 1

100 parts of ammonium paramolybdate, 2.8 parts of ammonium matavanadate and 9.2 parts of cesium nitrate were dissolved in 300 parts of pure water. This aqueous solution was stirred while adding thereto a solution with 8.2 parts of 85 wt % phosphoric acid dissolved in 10 parts of pure water and a solution with 1.1 parts of telluric acid dissolved in 10 parts of pure water, and the resulting mixture was heated to 95° C. Then, a solution with 3.4 parts of copper nitrate, 7.6 parts of ferric nitrate, 1.4 parts of zinc nitrate and 1.8 parts of magnesium nitrate dissolved in 80 parts of pure water was added. Furthermore, the mixture was stirred at 100° C. for 15 minutes.

The resulting slurry was dried, and 2 parts of graphite were added to 100 parts of this dried material and mixed together, and was molded into a ring-shaped material having an outer diameter of 5 mm, an inner diameter of 2 mm and a length of 3 mm in a tablet molder. Then, this tablet-molded product was calcined under a stream of air at 380° C. for 5 hours to obtain a catalyst (1).

The catalyst (1) had a composition of $Mo_{12}P_{1.5}Cu_{0.3}V_{0.5}Fe_{0.4}Te_{0.1}Mg_{0.15}Zn_{0.1}Cs_1$ in an atom ratio excluding oxygen.

A mixture of 370 mL of catalyst (1) and 130 mL of alumina ball having an outer diameter of 5 mm was packed in the material gas inlet of a steel fixed bed tubular reactor with the inner diameter of 25.4 mm comprising a heating medium bath, and 1,000 mL of catalyst (1) was packed in the outlet.

A material gas containing 5.5 vol % of methacrolein, 10.7 vol % of oxygen, 9.0 vol % of water vapor and 74.8 vol % of nitrogen was passed through the catalyst layer at a reaction temperature (temperature of the heating medium bath) of 282° C. and at a space velocity of 630 $hr^{-1}$. The reaction was carried out in the flow process under atmospheric pressure.

After 60 minutes from the starting of the reaction, the reaction product was collected and analyzed, and it was found that the conversion of methacrolein was 83.7%, and the selectivity of methacrylic acid was 83.8%.

The reaction was further continued for 2,400 hours under the conditions described above, and the reaction product was collected and analyzed, and it was found that the conversion of methacrolein was 83.6%, and the selectivity of methacrylic acid was 83.8%. The catalyst suffered almost no deterioration even after the reaction was carried out for 2,400 hours under these conditions.

Example 2

The reaction was carried out in the same manner as Example 1 except that a material gas containing 4.9 vol % of methacrolein, 10.3 vol % of oxygen, 9.0 vol % of water vapor and 75.8 vol % of nitrogen was passed through the catalyst layer at a reaction temperature (temperature of the heating medium bath) of 284° C. and at a space velocity of 710 $hr^{-1}$.

After 60 minutes from the starting of the reaction, the reaction product was collected and analyzed, and it was found that the conversion of methacrolein was 84.1%, and the selectivity of methacrylic acid was 84.0%.

The reaction was further continued for 2,400 hours under the conditions described above, and the reaction product was collected and analyzed, and it was found that the conversion of methacrolein was 83.9%, and the selectivity of methacrylic acid was 84.1%. The catalyst suffered almost no deterioration even after the reaction was carried out for 2,400 hours under these conditions.

Comparative Example 1

The reaction was carried out in the same manner as Example 1 except that a material gas containing 3.5 vol % of methacrolein, 8.8 vol % of oxygen, 6.5 vol % of water vapor and 81.2 vol % of nitrogen was passed through the catalyst layer at a reaction temperature (temperature of the heating medium bath) of 286° C. and at a space velocity of 1,000 $hr^{-1}$.

After 60 minutes from the starting of the reaction, the reaction product was collected and analyzed, and it was found that the conversion of methacrolein was 84.0%, and the selectivity of methacrylic acid was 84.2%.

The reaction was further continued for 2,400 hours under the conditions described above, and the reaction product was collected and analyzed, and it was found that the conversion of methacrolein was 81.2%, the selectivity of methacrylic acid was 84.4%, and the catalyst activity decreased significantly.

Comparative Example 2

The reaction was carried out in the same manner as Example 2 except that the material gas was changed to a material gas containing 4.9 vol % of methacrolein, 10.3 vol % of oxygen, 14.7 vol % of water vapor and 70.1 vol % of nitrogen.

After 60 minutes from the starting of the reaction, the reaction product was collected and analyzed, and it was found that the conversion of methacrolein was 83.8%, and the selectivity of methacrylic acid was 83.8%.

The reaction was further continued for 2,400 hours under the conditions described above, and the reaction product was collected and analyzed, and it was found that the conversion of methacrolein was 82.1%, the selectivity of methacrylic acid was 83.3%, and the catalyst activity decreased significantly.

Comparative Example 3

The reaction was carried out in the same manner as Example 2 except that the material gas was changed to a material gas containing 4.9 vol % of methacrolein, 10.3 vol % of oxygen, 2.0 vol % of water vapor and 82.8 vol % of nitrogen.

After 60 minutes from the starting of the reaction, the reaction product was collected and analyzed, and it was found that the conversion of methacrolein was 82.5%, and the selectivity of methacrylic acid was 83.1%.

The reaction was further continued for 2,400 hours under the conditions described above, and the reaction product was collected and analyzed, and it was found that the conversion of methacrolein was 80.1%, the selectivity of methacrylic acid was 83.5%, and the catalyst activity decreased significantly.

Example 3

100 parts of molybdenum trioxide, 3.2 parts of vanadium pentoxide and 6.7 parts of 85 wt % phosphoric acid were mixed with 800 parts of pure water. The resulting mixture was heated and stirred under reflux for 3 hours, and thereafter 0.5 parts of copper oxide, 0.7 parts of boric acid and 1.2 parts of germanium dioxide were added, and the resulting mixture was heated and stirred under reflux for 2 hours. The resulting slurry was cooled down to 50° C., and thereafter a solution with 11.2 parts of cesium bicarbonate dissolved in 30 parts of pure water was added, and the resulting slurry was stirred for 15 minutes. Then, a solution with 10 parts of ammonium nitrate dissolved in 30 parts of pure water was added, and the resulting slurry was stirred for 15 minutes.

The resulting slurry was dried, and 2 parts of graphite were added to 100 parts of this dried material and mixed together, and was molded into a ring-shaped material having an outer diameter of 5 mm, an inner diameter of 2 mm and a length of 3 mm by a tablet molder. Then, this tablet-molded product was calcined under a stream of air at 380° C. for 5 hours to obtain a catalyst (2).

The catalyst (2) had a composition of $Mo_{12}P_1Cu_{0.1}V_{0.6}Ge_{0.2}B_{0.2}Cs_1$ in an atom ratio excluding oxygen.

A mixture of 150 mL of catalyst (2) and 90 mL of alumina ball having an outer diameter of 5 mm was packed in the material gas inlet of a steel fixed bed tubular reactor with the inner diameter of 25.4 mm comprising a heating medium bath, a mixture of 200 mL of catalyst (2) and 40 mL of alumina ball having an outer diameter of 5 mm was packed in the central part, and 1,020 mL of catalyst (2) was packed in the outlet.

A material gas containing 5.2 vol % of methacrolein, 10.5 vol % of oxygen, 9.0 vol % of water vapor and 75.3 vol % of nitrogen was passed through the catalyst layer at a reaction temperature (temperature of the heating medium bath) of 282° C. and at a space velocity of 670 $hr^{-1}$. The reaction was carried out in the flow process under atmospheric pressure.

After 60 minutes from the starting of the reaction, the reaction product was collected and analyzed, and it was found that the conversion of methacrolein was 85.1%, and the selectivity of methacrylic acid was 85.0%.

The reaction was further continued for 2,400 hours under the conditions described above, and the reaction product was collected and analyzed, and it was found that the conversion of methacrolein was 85.0%, and the selectivity of methacrylic acid was 85.0%. The catalyst suffered almost no deterioration even after the reaction was carried out for 2,400 hours under these conditions.

INDUSTRIAL APPLICABILITY

According to the present invention, in a method of producing methacrylic acid which comprises subjecting methacrolein to gas phase contact oxidation with molecular oxygen using a reactor packed with a catalyst comprising a compound oxide containing molybdenum and phosphorus as essential components, deterioration of the catalyst can be effectively inhibited.

What is claimed is:

1. A method of producing methacrylic acid by passing a gas containing methacrolein, oxygen and water vapor through a reactor packed with a catalyst containing as the main component a compound oxide containing molybdenum and phosphorus, wherein a concentration of methacrolein in the gas is in a range of 4 to 6.5 vol %, a molar ratio of the water vapor to the methacrolein in the gas is in a range of 1 to 2, and a space velocity of the gas to the catalyst-packed layer is in a range of 500 to 750 $h^{-1}$.

2. The method of producing methacrylic acid according to claim 1 wherein the concentration of methacrolein in the gas is in a range of 4.5 to 6 vol %.

3. The method of producing methacrylic acid according to claim 1 wherein the molar ratio of water vapor to methacrolein in the gas is in a range of 1.5 to 1.9.

4. The method of producing methacrylic acid according to claim 1 wherein the space velocity of the gas to the catalyst-packed layer is in a range of 550 to 700 $h^{-1}$.

5. The method of producing methacrylic acid according to claim 1 wherein the catalyst has a composition expressed by the following general formula (I):

$$Mo_aP_bCu_cV_dX_eY_fO_g \qquad (I)$$

wherein Mo, P, Cu, V and O represent molybdenum, phosphorus, copper, vanadium and oxygen, respectively; X represents at least one element selected from the group consisting of iron, cobalt, nickel, zinc, magnesium, calcium, strontium, barium, titanium, chromium, tungsten, manganese, silver, boron, silicon, aluminum, gallium, germanium, tin, lead, arsenic, antimony, bismuth, niobium, tantalum, zirconium, indium, sulfur, selenium, tellurium, lanthanum and cerium; Y represents at least one element selected from the group consisting of potassium, rubidium, cesium and thallium; a, b, c, d, e, f and g each represents an atom ratio of each element, and when a=12, $0.1 \leq b \leq 3$, $0.01 \leq c \leq 3$, $0.01 \leq d \leq 3$, $0 \leq e \leq 3$ and $0.01 \leq f \leq 3$; and g represents a ratio of an oxygen atom required for satisfying a valence of each component.

* * * * *